(12) United States Patent  (10) Patent No.: US 8,272,250 B2
Wang et al.  (45) Date of Patent: Sep. 25, 2012

(54) NANOPARTICLE ARRAY SENSORS

(75) Inventors: Shiliang Wang, Cypress County (CA); David Pedersen, Medicine Hat (CA)

(73) Assignee: Her Majesty the Queen as represented by the Minister of National Defence of Her Majesty's Canadian Government, Ottawa, Ontario (CA)

( * ) Notice: Subject to any disclaimer, the term of this patent is extended or adjusted under 35 U.S.C. 154(b) by 470 days.

(21) Appl. No.: 12/385,691

(22) Filed: Apr. 16, 2009

(65) Prior Publication Data
US 2010/0263435 A1  Oct. 21, 2010

Related U.S. Application Data

(60) Provisional application No. 61/071,172, filed on Apr. 16, 2008.

(51) Int. Cl.
*G01N 27/04* (2006.01)
(52) U.S. Cl. ........................ 73/31.05; 977/777; 977/957
(58) Field of Classification Search ........................ None
See application file for complete search history.

(56) References Cited

U.S. PATENT DOCUMENTS
6,537,498 B1 * 3/2003 Lewis et al. ................ 422/82.01

OTHER PUBLICATIONS

Shipway, A. N., Katz, E. and Willner, I. (2000), Nanoparticle Arrays on Surfaces for Electronic, Optical, and Sensor Applications. ChemPhysChem, 1:18-52. doi: 10.1002/1439-7641(20000804)1:1<18::AID-CPHC18>3.0.CO;2-L.*
Colloidal Metal—Insulator—Metal Ensemble Chemiresistor Sensor. Hank Wohltjen, Arthur W. Snow. Analytical Chemistry 1998 70 (14), 2856-2859.*

* cited by examiner

*Primary Examiner* — Hezron E Williams
*Assistant Examiner* — Mark A Shabman
(74) *Attorney, Agent, or Firm* — George A. Seaby

(57) ABSTRACT

An effective sensor for indicating exposure to a toxic gas includes a non-conductive, inert substrate such as glass or polyethylene, a two-dimensional film of nanoparticles of a conductive metal such as silver or copper on the substrate and an electrode connected to each end of the film. When an electrical current passes through the film and the sensor is exposed to a toxic gas, changes in the electrical resistance of the film provides an indication of the presence of the toxic gas.

18 Claims, 3 Drawing Sheets

NANOPARTICLE ARRAY SENSORS

This application claims priority on U.S. Provisional Application 61/071,172 filed Apr. 16, 2008.

BACKGROUND OF THE INVENTION

1. Field of the Invention

This invention relates to a sensor for use in an indicator to provide a warning of exposure to a toxic gas, and to a method of producing such a sensor.

2. Description of Related Art

Personal badge-type exposure indicators are critical components of next generation protective gear. Ideally, such indicators not only warn of an exposure event but also quantify the extent of exposure and provide a stream of data in real time so that informed decisions can be made regarding ambient toxicity.

The inventors have determined that a film of naked nanoparticles on a non-conductive substrate such as glass or polyethylene is a suitable sensor for use in an indicator of the type for use with protective gear.

The current flow between metal nanoparticles interconnected by molecules is a fundamental process underlying single electron transistors and much of the field of molecular electronics. When the distance between nanoparticles is greater than 2 nm and the barrier to charge transfer greater than 1 eV, current flow between particles occurs via single-electron tunneling. Under these conditions, the residence time of the electron on a nanoparticle is relatively long and electric current flow occurs via a series of discrete tunneling "hops" of electrons from nanoparticle to nanoparticle. In this regime, the rate of current flow depends on a number of factors including the bias applied, the electronic structure of the interparticle molecules, the goodness of the electrical contact between the molecules and the surface of the nanoparticles, the distance between nanoparticles and the charging energy of the nanoparticles.

Current flow through monolayers of close-packed metal nanoparticles have been extensively studied. Examples studied to date include films of thiol-capped 2.7-4.8 nm diameter Ag nanoparticles, and monolayer-protected gold nanoparticles. The nanoparticles in such films are typically encapsulated in monolayer coatings, which prevent particle coalescence as well as retain a constant and well defined interparticle spacing. The formation of films from the coated nanoparticles occurs via self-assembly. The resulting bilayer of molecules between the nanoparticles in such films provides a barrier to direct charge transport between particles, ensuring that interparticle, single-electron tunneling of charge across the molecular bridge between the nanoparticles is the dominant charge transfer mechanism. In this configuration, the conduction characteristics of the nanoparticle film are expected to be especially sensitive to the nature of the molecular bridge. Self-assembly methods, however, are not ideally suited for study of the molecular bridge because changing the type of bridge also changes the interparticle spacing so the results are convoluted.

BRIEF SUMMARY OF THE INVENTION

To circumvent the above mentioned problem the inventors focused on films of naked nanoparticles. Using a gas-phase deposition approach, monolayers of ligand-free nanoparticles can be generated in which the average interparticle distance is controllable. When the interparticle distance is small enough, these naked nanoparticle films also display conduction behaviors characteristic of single-electron tunneling through the spaces between the particles. Because the electrons necessarily tunnel through the interparticle space, the addition of molecular material to these spaces (most likely as an adsorbate on the nanoparticle surfaces) impacts the tunneling rate and current flow observed. Thus, the medium, through which the electron tunnels, can be changed without changing the interparticle spacing.

As mentioned above, the inventors have determined that a film of naked metal nanoparticles on a glass or polyethylene substrate is a suitable sensor for use in an indicator of the type for use with protective gear. As a specific example, the resistance across an Ag nanoparticle film changes when the film is exposed to a toxic gas such as 2-chloroethyl ethyl sulfide (CIEES), which is a simulant for mustard gas. The same is true when the film is exposed to sulfur mustard gas or HCN warfare agent.

In accordance with one aspect, the present invention provides a method of producing a sensor for use as an indicator of exposure to a toxic gas comprising the steps of: generating nanoparticles of a conductive metal; depositing the nanoparticles on a non-conductive inert substrate to yield a two-dimensional film of nanoparticles, wherein the spacing between the nanoparticles is small enough to permit electron tunneling between particles and a current can be made to flow across the film; and connecting an electrode to each end of the film, whereby, when an electrical current is passed through the film and the sensor is exposed to a toxic gas, changes in the electrical resistance of the film will provide an indication of the presence of such toxic gas.

In accordance with a second aspect, the present invention provides a sensor for use as an indicator of exposure to a toxic gas comprising: a non-conductive, inert substrate; a two-dimensional film of nanoparticles of a conductive metal on said substrate, wherein the spacing between the nanoparticles is small enough to permit electron tunneling between particles and a current can be made to flow across the film, whereby, when an electrical current is passed through the film and the sensor is exposed to a toxic gas, changes in the electrical resistance of the film will provide an indication of the presence of such toxic gas.

Using the above defined method, arrays of naked nanoparticles have been made with interparticle spacing small enough that electrons can tunnel between particles and a current can be made to flow through the nanoparticle film. The rate of electron tunneling across the film is extremely sensitive to the nature of the material between the nanoparticles. Adsorption of any species on or near the nanoparticles causes a large change in conductance of the interparticle gaps. The measured resistance of the film or tunneling current is a sensitive means of sensing the presence of adsorbate.

The particles are naked and the particle spacing is controlled. Because the particles are naked, there is dependence on matrix material, and tailor-designing matrices that respond to specific chemicals is not required. Any gases that adsorb to the nanoparticles can be detected, and it should be possible to determine the nature of the adsorbed gas from changes in conductance characteristics of the film.

BRIEF DESCRIPTION OF THE DRAWINGS

The invention is described in greater detail below with reference to the accompanying drawings, wherein.

DETAILED DESCRIPTION OF THE INVENTION

Figure 1:
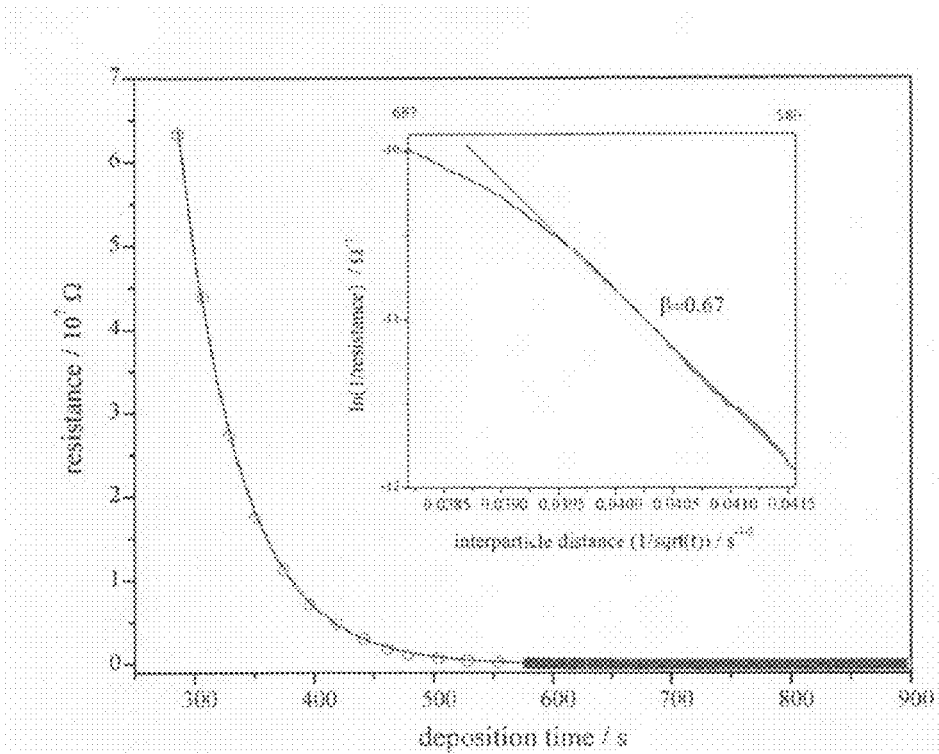
FIG. 1 is a plot of resistance between two Ag electrodes on a polyethylene (PE) film versus deposition time.
Figure 2:
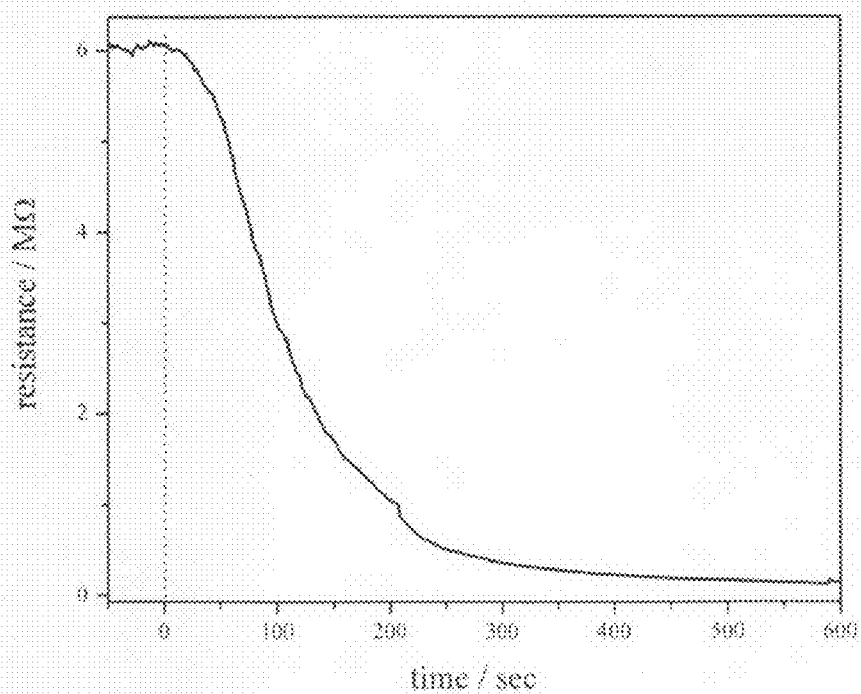
FIG. 2 is a plot of resistance between two Ag electrodes on a PE film versus time of exposure to CIEES.
Figure 3:
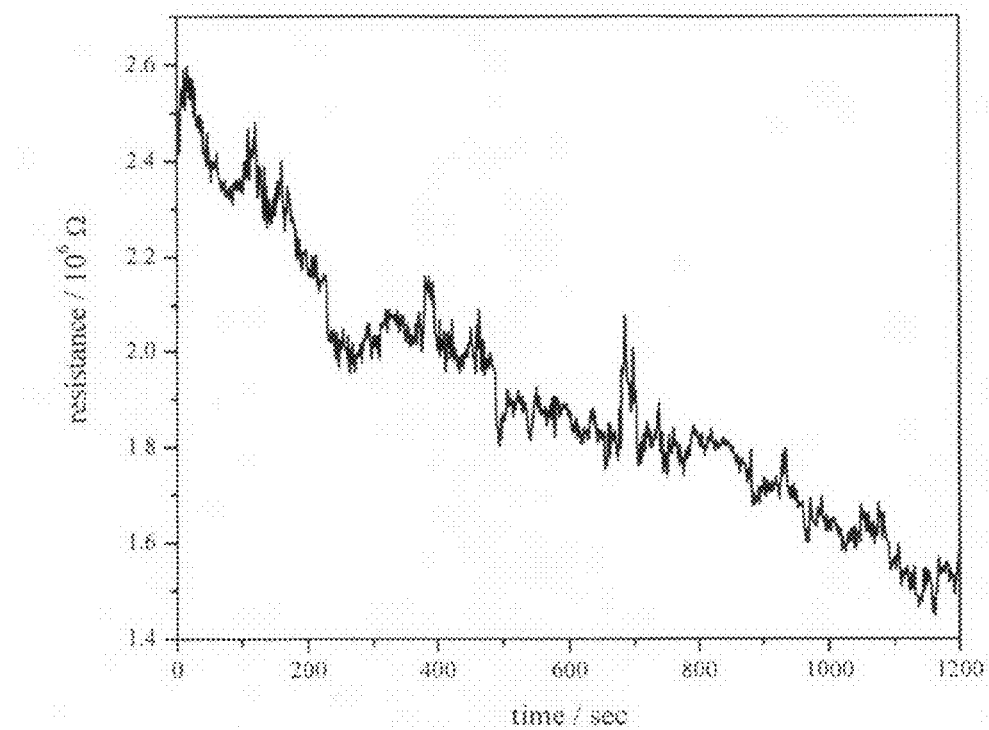
FIG. 3 is a plot of resistance across an Ag nanoparticle film as a function of exposure time to CIEES.
Figure 4:
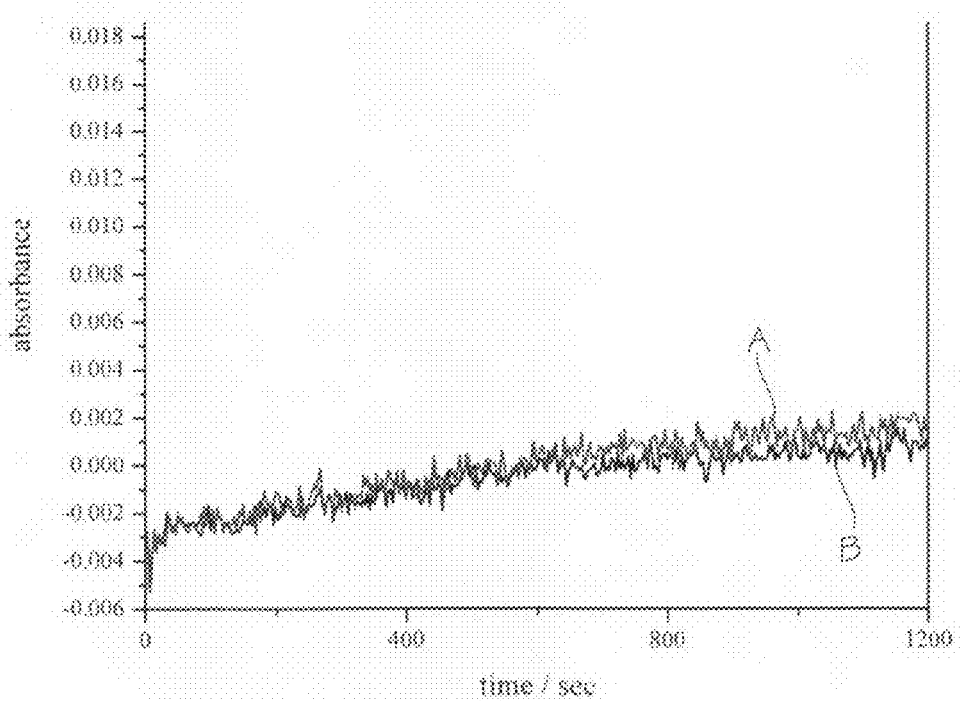
FIGS. 4 and 5 are plots of absorbance of the Ag nanoparticle film as a function of exposure time to CIEES and wavelength, respectively, the absorbance data being acquired simultaneously with the resistance data shown in FIG. 3.
Figure 5:
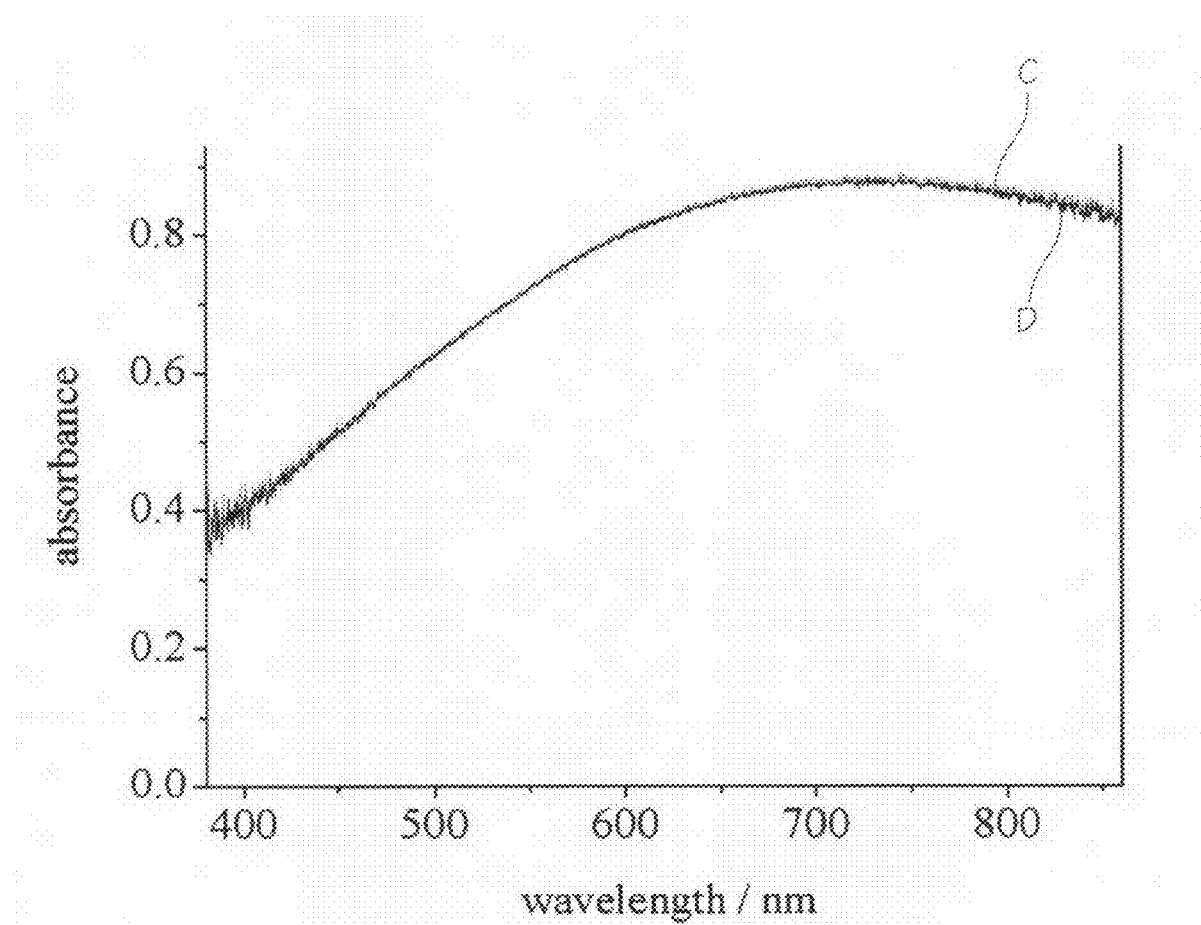

The inventors deposited nanoparticles on a substrate using a deposition apparatus described elsewhere (see Pedersen, D. B. et al, J. Phys. Chem. C., 111 (15), 5592-5598). Nanoparticles were first generated in the gas phase using a magnetron DC-sputtering source. Application of a 280 V bias between an anode cap and a metal target caused a discharge in the 0.17 Torr pressure of Ar gas maintained between them. The current flow to the discharge was kept to 200 mA. Any $Ar^+$ ions generated in the discharge were accelerated toward the negatively biased metal target which they struck with force, thus liberating metal atoms to the gas phase. These atoms were swept up in the flow of Ar leaving the discharge region. Upon leaving the sputtering region the atoms passed through an aggregation zone where the collision frequency between metal atoms was high, and formation of nanoparticles occurred. The nanoparticles thus generated them moved downstream into the expansion zone, which was evacuated by a 500 L $s^{-1}$ turbo pump (Varian V-550). The nanoparticles then passed through an orifice into the neighboring deposition chamber where a pressure of <$10^{-4}$ Torr was maintained during deposition by a 300 L $s^{-1}$ turbo pump (Varian TV-301). The size of the nanoparticles could be varied by varying parameters such as Ar and He gas flow rates, aggregation zone length and discharging current. A substrate (polyethylene or glass) with painted silver electrodes positioned in front of the orifice collected the nanoparticles which deposited as 2D films of naked nanoparticles. The distance between the particles varied with deposition time pseudo-continuously; at longer times more particles reside on the surface and the average interparticle distance is decreased accordingly. The resistance between electrodes was monitored during deposition with an Agilent digital multimeter (34401A) connected to a computer via HPIB interface.

Exposure experiments were conducted in a fume hood. A nanoparticle-coated polyethylene film was placed on a stand. Light exiting an optic fiber connected to a halogen lamp passed through the sample and was collected by a collimating lens attached to a second optic fiber, on the other side of the sample, that carried the light to the CCD array of a UV-vis spectrometer (Ocean Optics SD2000). In this configuration, the resistance between electrodes and the spectrum of the nanoparticles between electrodes could be monitored simultaneously during exposure of the nanoparticle film to CIEES. Exposure was effected by opening a bottle of CIEES (Aldrich, 98%) 5 cm from the film and letting the vapors diffuse in the fume hood.

The nanoparticle sensor was also exposed to sulfur mustard gas and HCN warfare agent, and the sensor responded well to both. The sensor was exposed to CO and there was no response which demonstrates some selectivity.

The deposition of Ag nanoparticles generated by the sputtering source onto substrates yielded two dimensional arrays of nanoparticles. A sample scanning tunneling microscope (STM) image of a film deposited on highly ordered pyrolitic graphite (HOPG) revealed particles appearing as white shapes against a darker background. The outline of each particle is discernible and the size easily determined. From such images the 2D nature of the films was established and the diameter of the nanoparticles was found to be 2.8±0.5 nm. The distance between particles could be varied by varying the deposition time. The distance between the nanoparticles was found to be >10 nm but smaller interparticle separation was possible by increasing the deposition time. In general, the interparticle separation has a well defined average value because the deposition is a random process. It is straightforward to show that a random deposition yields an average interparticle separation that varies inversely with $t^{1/2}$, where t is the deposition time. Accordingly, plots of the interparticle distance versus the inverse of the square root of the deposition time are linear (see Pedersen et al supra). The linearity combined with STM data and trends in the optical properties of such films establish that the films are 2D arrays of nanoparticles with interparticle distances that decrease steadily as deposition time is increased.

For a 15 min deposition of Ag nanoparticles on a glass slide or polyethylene film, the average interparticle distance is small enough that current can flow between two silver electrodes situated at either end of the nanoparticle film. When the particle density is low enough, such current is expected to flow via tunneling of electrons across the interparticle gaps. Controlling the distance between adjacent nanoparticles affords an opportunity to examine the distance dependence of the through-space tunneling current between nanoparticles. A plot of the resistance, measured between two silver electrodes spaced 3 mm apart on the surface of a polyethylene film, versus t is shown in FIG. 1. The resistance data were obtained between two Ag electrodes painted onto a 5 μm thick polyethylene film. The electrodes were 3 mm apart. For each point in the early part of the deposition, the sputtering source was turned off so that the current flow associated with the deposition of the 3.2±0.5 nm diameter Ag nanoparticle ions onto the polyethylene film did not affect the resistance measured. After 580 s, data were obtained continuously with the source on because this effect was negligible. In the inset, the portion of the curve where ln(resistance$^{-1}$) versus the deposition time is linear is shown. A fit to the tunneling expression is shown as a solid, straight line. These data were collected in situ during deposition of the nanoparticles on the polyethylene surface. Similar results were obtained on glass. Early on in the deposition the resistance is infinite. As the particle density in the film increases it eventually reaches a critical value where a resistance and current flow is measurable. The average spacing between nanoparticles (i.e. outer edge to outer edge) at this time is 6.0±0.5 nm, as determined by scanning tunneling microscopy (STM) imaging of nanoparticles deposited on highly oriented pyrolytic graphite (HOPG) under identical conditions. At this distance, there is no direct, conducting path for electrons to follow and current flow occurs via tunneling of electrons between adjacent nanoparticles. As the distance between particles decreases further the tunneling rate increases and the resistance measured between electrodes decreases, as seen in FIG. 1.

The tunneling current, or rate of tunneling, is given by $$I = I_0 e^{-\beta d}$$

where $I_0$ is the pre-exponential factor, d is the interparticle separation, and β is the fall-off or attenuation factor. A fit of this equation to the inverse of the resistance is shown in the inset of FIG. 1. In the 26-150 k'Ω region the fit is good indicating that the tunneling distance between adjacent nanoparticles decreases steadily during this stage of the deposition. To establish a fit requires determining the proportionality factor A for $d=At^{-1/2}$, which was done by measuring interparticle distance d at specific time t using STM imaging of Ag nanoparticles on HOPG. The value of A obtained is expected to hold over a certain range of deposition times. Accordingly, the fit is good in the 26-150 k'Ω region but not elsewhere. From such fits to a number of data sets, the value of β obtained is 0.67 Å$^{-1}$. This value compares well with literature values that are typically 0.6-1.0 Å$^{-1}$ (see Adams, D. M. et al, J. phys. Chem. B, 107 (28), 663-6997). The good comparison indicates that tunneling is the dominant mechanism of charge transport in the nanoparticle films with comparable interparticle separations.

The addition of molecules to the interparticle spaces is expected to change the rate of tunneling and thus the resistance of the nanoparticle film. To effect such change, the nanoparticles were exposed to CIEES. A sample of the change in film resistance that resulted during the exposure is shown in FIG. 2. As seen, within 1 min of opening a bottle of CIEES positioned 5 cm away, in a fume hood through which air was flowing at a rate greater than 500 $ft^3\ min^{-1}$ with the electrodes 3 mm apart, the resistance across the film had changed. Furthermore, the resistance decreased from 6 M'Ω to 160 k'Ω within 8 min. The large change suggests high sensitivity.

To gauge the sensitivity, the change in resistance and the change in the optical properties of some nanoparticle films were monitored simultaneously. Some sample results of the optical and resistance data obtained are shown in FIGS. 3 to 5. FIG. 3 shows the resistance data across an Ag nanoparticle film. The resistance data were acquired simultaneously with the absorbance data shown in FIGS. 4 and 5. Lines A and B in FIG. 4 show changes in the absorbance measured at 700 and 650 nm, respectively as a function of exposure time t. In FIG. 5, the absorbance spectrum is shown before (line C) and after (line D) the exposure.

Following exposure to CIEES, the resistance of the nanoparticle films decreased significantly, as seen in FIG. 3, and stayed there. The effect was irreversible. Heating of the films was not possible because the polyethylene melts and swells at relatively low temperatures, which would drastically alter the interparticle spacing and conduction characteristics of the nanoparticle film. Letting the films off-gas by leaving the films to sit for several days had no effect; CIEES irreversibly adsorbed to the nanoparticles. In this context, the nanoparticle films function as cumulative sensors. Exposure of such sensors to trace amounts of toxic chemicals such as CIEES results in a steady build up of the toxic chemical on the surfaces of the nanoparticles. Eventually, the build up causes a change in resistance large enough to be measured. The disadvantage of cumulative sensing is that the sensor is destroyed in the process. The advantage is that cumulative sensors can detect trace quantities of toxic gas well below the detection threshold of concentration-based, one-time sampling techniques. Furthermore, the cumulative sensor response changes steadily with time thus providing a continuous readout related to the total amount of toxic chemical that the sensor has encountered over the total period of exposure. Accordingly, the sensor reading is directly related to concentration-time (CT) values used in determining the toxicity effect on personnel exposed to warfare agents and other toxic chemicals. In light of these sensing properties and the highly portable nature of the nanoparticle films, measurements of resistance across these films is useful as a portable sensor platform suitable for use as personal exposure indicators and other related devices.

The method described above has been used to deposit copper nanoparticles on an inert substrate, i.e. glass and polyethylene. Sensors can also be produced using any noble metal such as gold, platinum and palladium. The particle size and spacing of the nanoparticles are listed hereinbefore as 3.2 and 6.0, respectively. However, it has been determined that the particle size can be 1-100 nm and preferably 2-50 nm, and the edge to edge spacing can be 4 to 50 nm and preferably 5 to 25 nm.

The invention claimed is:

1. A method of producing a sensor for use as an indicator of exposure to toxic gas comprising the steps of:

generating naked, conductive metal nanoparticles;

depositing the naked nanoparticles on a non-conductive, inert substrate to yield a two-dimensional film of the naked, conductive metal nanoparticles, wherein the spacing between the nanoparticles is small enough to permit electron tunneling between particles and a current can be made to flow across the film; and connecting an electrode to each end of the film, whereby, when an electrical current is passed through the film and the sensor is exposed to a toxic gas, changes in the electrical resistance of the film will provide an indication of the presence of such toxic gas.

2. The method of claim 1, wherein the conductive metal is selected from the group consisting of silver, copper, gold, platinum and palladium, and the substrate is glass or polyethylene.

3. The method of claim 2, wherein the conductive metal is silver and the substrate is a polyethylene film.

4. The method of claim 2, wherein the diameter of the nanoparticles is 1 to 100 nm.

5. The method of claim 2, wherein the diameter of the nanoparticles is 2 to 50 nm.

6. The method of claim 3, wherein the diameter of the nanoparticles is approximately 2.8-3.2±0.5 nm.

7. The method of claim 5, wherein the spacing between the nanoparticles is 4 to 50 nm.

8. The method of claim 5, wherein the spacing between the nanoparticles is 5 to 25 nm.

9. The method of claim 6, wherein the spacing between the nanoparticles is 6.0±0.5 nm.

10. A sensor for use as an indicator of exposure to a toxic gas comprising:

a non-conductive, inert substrate;

a two-dimensional film of naked, conductive metal nanoparticles on said substrate, wherein the spacing between the nanoparticles is small enough to permit electron tunneling between particles and a current can be made to flow across the film, whereby, when an electrical current is passed through the film and the sensor is exposed to a toxic gas, changes in the electrical resistance of the film will provide an indication of the presence of such toxic gas.

11. The sensor of claim 10, wherein the conductive metal is selected from the group consisting of silver, copper, gold, platinum and palladium, and the substrate is glass or polyethylene.

12. The sensor of claim 11, wherein the conductive metal is silver and the substrate is a polyethylene film.

13. The sensor of claim 11, wherein the diameter of the nanoparticles is 1 to 100 nm.

14. The sensor of claim 11, wherein the diameter of the nanoparticles is 2 to 50 nm.

15. The sensor of claim 12, wherein the diameter of the nanoparticles is approximately 2.8-3.2±0.5 nm.

16. The sensor of claim 14, wherein the spacing between the nanoparticles is 4 to 50 nm.

17. The sensor in claim 14, wherein the spacing between the nanoparticles is 5 to 25 nm.

18. The sensor of claim 15, wherein the spacing between the nanoparticles is 6.0±0.5 nm.

* * * * *